(12) United States Patent
Fattal et al.

(10) Patent No.: US 8,134,702 B1
(45) Date of Patent: Mar. 13, 2012

(54) OPTICAL DEVICES FOR SURFACE ENHANCED RAMAN SPECTROSCOPY

(75) Inventors: David A. Fattal, Mountain View, CA (US); Zhiyong Li, Redwood City, CA (US); Qiangfei Xia, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 206 days.

(21) Appl. No.: 12/574,379

(22) Filed: Oct. 6, 2009

(51) Int. Cl.
   *G01J 3/44* (2006.01)
(52) U.S. Cl. ....................................... 356/301
(58) Field of Classification Search ................ 356/301, 356/72–73
   See application file for complete search history.

(56) References Cited

U.S. PATENT DOCUMENTS 6,985,223 B2   1/2006   Drachev et al.
2008/0024776 A1 *  1/2008   Bratkovski et al. ........... 356/301

OTHER PUBLICATIONS

Xia et al. "Fab of Sub-25nm Diameter Pillar Nanoimprint Molds with Smooth Sidewalls Using Self-Perfection by Liquefaction & Reactive Ion Etching",Nanotechnology 19(2008) pp. 1-4.
Chou et al. "Improved Nanofabriction Through Guided Transient Liquefaction", Nature Nanotechnology, vol. 3, May 2005, pp. 295-300.
Merlein et al. "Nanomechanical Control of an Optical Antenna", Nature Photonics, vol. 2, Apr. 2008, pp. 230-233.
Penmetsa et al."Design & Modeling of a Tubable Opt Antenna Enabled by a Micromachined Actuator", Proceedings 2009 4th IEEE Intl Conf. Jan. 5-8, 2009,Shenzhen, China, pp. 176-180.
Fischer et al. "Engineering the Optical Response of Plasmonic Nanoantennas", Optics Express, vol. 16, No. 12, Jun. 6, 2008, pp. 9144-9154.

* cited by examiner

*Primary Examiner* — Tarifur Chowdhury
*Assistant Examiner* — Abdullahi Nur

(57) ABSTRACT

An optical device for surface enhanced Raman spectroscopy includes a substrate, and at least one antenna established thereon. The at least one antenna including at least two segments, where each segment is formed of a metal having a predetermined volume and a predetermined contact angle with respect to the substrate. A gap is located between the two segments. The gap has a controllable size such that the at least one antenna resonates at a predetermined frequency that corresponds with the gap.

16 Claims, 4 Drawing Sheets

OPTICAL DEVICES FOR SURFACE ENHANCED RAMAN SPECTROSCOPY

STATEMENT REGARDING FEDERALLY SPONSORED RESEARCH OR DEVELOPMENT

This invention was made in the course of research partially supported by a grant from The Defense Advanced Research Projects Agency, Grant No. HR0011-09-3-0002. The U.S. government has certain rights in the invention.

BACKGROUND

The present disclosure relates generally to optical devices for surface enhanced Raman spectroscopy.

Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species. As such, Raman spectroscopy is a useful technique for a variety of chemical or biological sensing applications. However, the intrinsic Raman scattering process is very inefficient, and rough metal surfaces, various types of nano-antennas, as well as waveguiding structures have been used to enhance the Raman scattering processes (i.e., the excitation and/or radiation process described above). This field is generally known as surface enhanced Raman spectroscopy (SERS).

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

The embodiments of the method disclosed herein advantageously enable control over the gap size during fabrication of, and in some instances after fabrication of, an antenna used, for example, in Raman spectroscopy. By controlling the materials and geometries used during fabrication, the resulting gap size may be readily controlled at least until equilibrium is reached. In one embodiment, the method disclosed herein allows gap size dimensions to be obtained that are otherwise believed to be unattainable via other processes, such as, for example, via lithography techniques. The smaller gap size enhances the electric field in the gap (i.e., the hot spot), and thus the electric field is much stronger than that of the incident electromagnetic (EM) wave in a certain frequency range around the resonant frequency of the antenna. When a material of interest (or an object made of the material of interest) is placed at the hot spot, the Raman scattering of this material is greatly enhanced.

Figure 1:
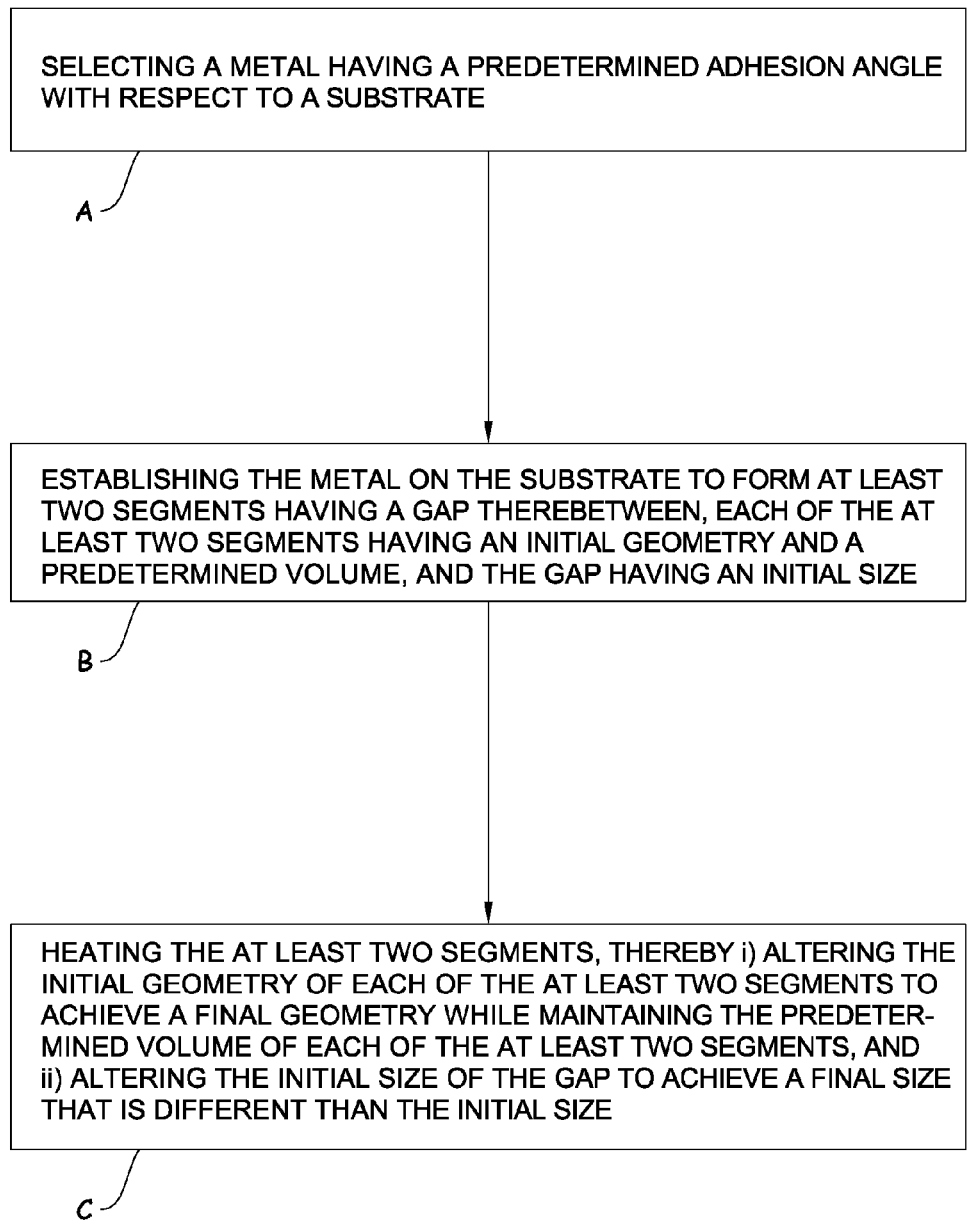
FIG. 1 is a flow diagram of an embodiment of a method for making an embodiment of an optical device.

Referring now to FIG. 1, an embodiment of a method for making an optical antenna is illustrated. Very generally, the method includes selecting a metal that has a predetermined contact angle with respect to a selected substrate, as shown at reference letter A. The metal is established on the substrate such that at least two segments are formed having a gap therebetween, as shown at reference letter B. The at least two segments are heated, as shown at reference letter C, which alters the geometry of the antenna and the size of the antenna gap. It is to be understood that the various embodiments of the method will be discussed further herein in reference to FIGS. 2 through 6.

Figures 2A, 2B:
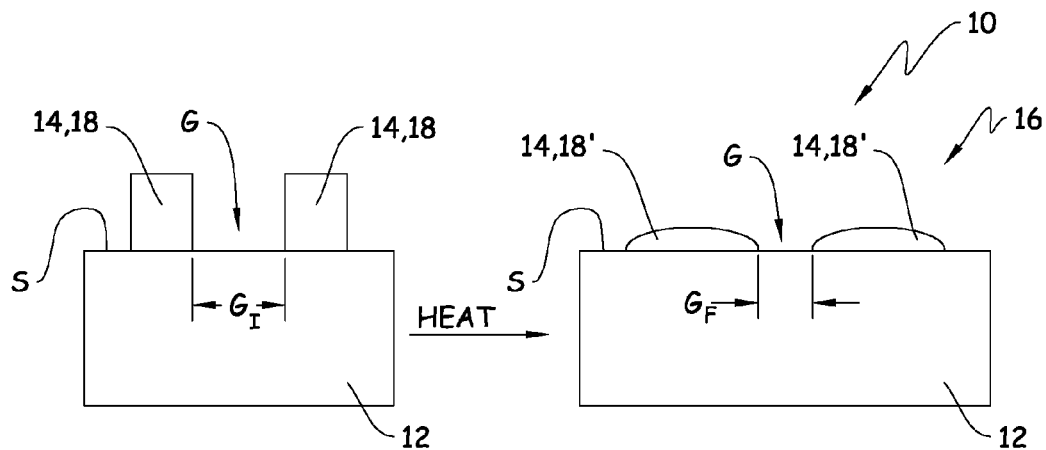
FIGS. 2A and 2B are schematic side views illustrating a metal established on a substrate (FIG. 2A), and the antenna formed after heating of the metal (FIG. 2B)
Figures 3A, 3B:
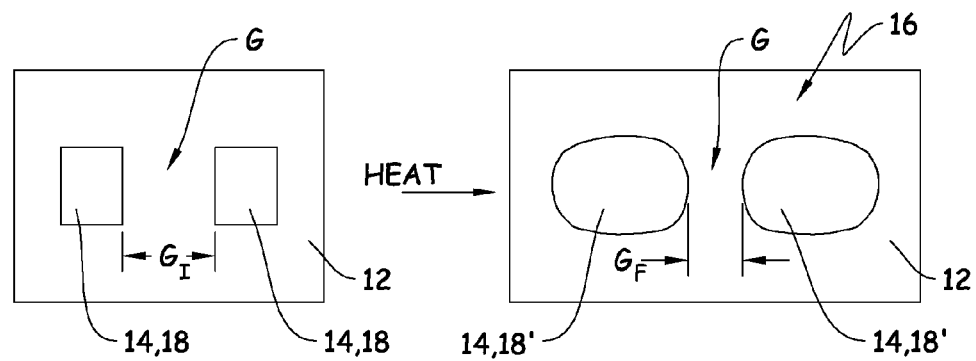
FIGS. 3A and 3B are top views of FIGS. 2A and 2B, respectively.
Figure 4:
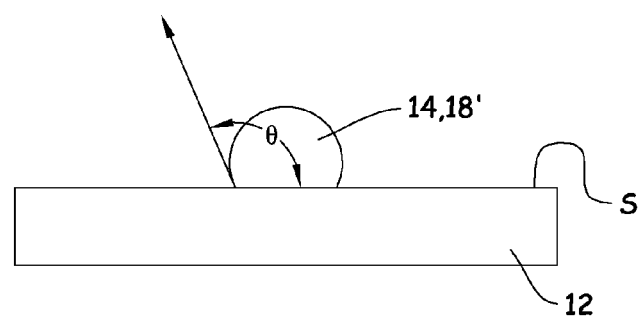
FIG. 4 is a schematic side view of a metal established on a substrate prior to heating, where the contact angle is illustrated.

Referring now to FIGS. 2A and 2B and 3A and 3B, side and top views of one embodiment of the method for forming an embodiment of the device 10 are respectively depicted. At the outset of the method, as shown in FIGS. 2A and 3A, both a substrate 12 and a metal 14 are selected. Non-limiting examples of suitable substrate 12 materials include single crystalline silicon, germanium, polymeric materials (acrylics, polycarbonates, polydimethylsiloxane (PDMS), polyimide, etc.), metals (aluminum, copper, stainless steel, alloys, etc.), quartz, ceramic, sapphire, silicon nitride, silicon dioxide, and glass.

The metal 14 selected will depend, at least in part, upon the substrate 12 selected (or vice versa). Generally, the metal 14 is a Raman active material (e.g., noble metals such as gold and silver). Suitable Raman active materials include those metals whose plasma frequency falls within the visible domain, and which are not too lossy (i.e., causing undesirable attenuation or dissipation of electrical energy). The plasma frequency depends on the density of free electrons in the metal, and corresponds to the frequency of oscillation of an electron sea if the free electrons are displaced from an equilibrium spatial distribution. In the embodiments disclosed herein, the metal 14 selected also has a predetermined contact angle θ (see, for example, FIG. 4) with respect to a surface S of the substrate 12. The contact angle θ is the angle at which a liquid/vapor interface (of the metal 14) meets a solid surface (e.g., substrate 12). It is to be understood that the contact angle θ at least partially controls the final geometry of the metal 14 (i.e., segments 18', shown in FIGS. 2B and 3B), and thus the selected substrate 12 and metal 14 depend, at least in part, upon the desirable gap size and geometry of the resulting antenna 16 (shown in FIGS. 2B and 3B).

Once the substrate 12 and metal 14 are selected, the metal 14 is established on the substrate surface S. The metal 14 is initially established with an initial volume and an initial geometry. It is to be understood that the initial volume is conserved throughout the process, while the initial geometry is changed. The initial geometry includes at least two segments 18 having a gap G therebetween. It is to be understood that the gap G of the initial geometry has an initial gap size $G_I$. As a result of further processing (described further hereinbelow), the initial gap size $G_I$ and the initial geometry of the segments 18 are altered so that a desirable final gap size $G_F$ and geometry of the segments 18' (shown in FIGS. 2B and 3B) are obtained. As shown in the embodiments of FIGS. 2A and 2B and 3A and 3B, the final gap size $G_F$ is larger than the initial gap size $G_I$.

Two segments 18, 18' are illustrated in each of the Figures discussed herein. While not shown, it is to be understood that the segments 18 may be positioned in a triangular arrangement, a flower petal arrangement, or another multi-segment configuration. All of the suitable segment configurations have the gap G positioned at the center of the segments 18, 18'.

In one embodiment, the initial geometric pattern of the segments 18 and the initial gap size $G_I$ are formed by nanoimprint lithography, electron-beam lithography, photo-lithography, extreme ultraviolet (EUV) lithography, X-ray lithography, any other suitable lithography technique, or any other pattern defining technique. In another embodiment, the initial geometric pattern of the segments 18 and the initial gap size $G_I$ are formed by depositing the desirable metal 14 and etching the metal 14 to pattern the segments 18. In still another embodiment, the initial geometric pattern of the segments 18 and the initial gap size $G_I$ are formed by depositing the desirable metal 14 and then using a lift-off technique to pattern the segments 18 from the deposited metal 14. In yet other embodiments, the initial geometric pattern of the segments 18 and the initial gap size $G_I$ are formed by direct deposition using focused ion beam or plating. The examples provided herein are illustrative and are by no means an exhaustive list.

After the segments 18 (having the initial geometry) are formed on the substrate surface S, at least the segments 18 are exposed to heating to form the antenna 16 and the device 10 (shown in FIGS. 2B and 3B). Heating may be accomplished isothermally (e.g., via conventional heating in an oven or furnace) or transiently (e.g., via pulsed laser heating). The temperature at which, and amount of time during which, heating takes place may vary, depending upon the selected metal 14 and the amount of metal 14 present.

Heating causes the metal segments 14, 18 to soften or melt, thereby rending them pliable. As such, the minimum heating temperature and/or time is at least sufficient to initiate melting of the metal 14. In a non-limiting example, the minimum heating time is about 100 nanoseconds.

The surface tension causes the molten metal 14 to flow, thereby causing segments 18 to change shape in a predetermined manner, thereby ultimately forming segments 18' and antenna 16. As shown in FIGS. 2B and 3B, the substrate 12 and the metal 14 may be selected so that upon heating, the metal 14 spreads out (length- and/or width-wise) such that the resulting segments 18' are thinner or flatter than segments 18, and the size of the gap G becomes smaller than the initial gap size $G_I$.

Heating may be achieved until a desirable final gap size $G_F$ is achieved and/or until the metal 14 and substrate 12 reach a state of equilibrium. In other words, the surface energy between the metal 14 and the substrate 12 reaches a minimum, and the metal 14 does not move anymore. As such, upon reaching equilibrium, heating no longer affects the geometry of the segments 18' (i.e., there is no appreciable effect on the gap size).

If the desired final gap size $G_F$ is equivalent to the gap size when the metal 14 and substrate 12 are in an equilibrium state, heating may be accomplished until a change in the geometry is no longer observed. In this embodiment, the gap size is predetermined, and is based upon the initial geometry, and the metal 14 and substrate 12 material selection. In other embodiments, however, heating may be stopped prior to reaching equilibrium. This may be accomplished when the desired final gap size $G_F$ is equivalent to a gap size that is larger than the size of the gap G corresponding with the equilibrium state. It is to be understood that since the gap size may be modified until equilibrium is reached, the gap G may be dynamically controlled (i.e., changed when desirable, even after initial fabrication) until equilibrium is reached. As such, the device 10 may have one or more final gap sizes $G_F$ and segment 18' geometries (i.e., they may be altered one or more times) prior to reaching the equilibrium state. For example, during device 10 fabrication, the initial gap size $G_I$ may be 20 nm, and then heating may be accomplished so that the final gap size $G_F$ is equivalent to 15 nm. This device 10 may be used in Raman spectroscopy, and will resonate at a frequency that corresponds with the resulting geometry of the segments 18' and the final gap size. Since the device 10 is not yet at equilibrium, it may be desirable to further alter the device 10 to resonate at another frequency. In this particular example, the device 10 may be reheated to alter the segment 18' geometry and gap size. As discussed herein, such alterations may take place until an equilibrium state is reached.

When it is desirable to control the gap G size dynamically, it is to be understood that the equilibrium may be altered by introducing, for example, a coating on the substrate 12 or a dopant into the metal 14. The introduction of such materials changes the surface tension, and as a result, changes the flow properties of the metal 14 upon exposure to heating. These additional parameters may be altered multiple times in order to dynamically control the gap G size.

In one non-limiting example, two Au cubes, each 100 nm in size (i.e., 100 nm length, width and height), are established (e.g., via lithography) on a $SiO_2$ surface 50 nm apart. Exposing these cube structures 14, 18 to heating causes them to melt into two spherical shaped particles 14, 18', each with a radius of 63 nm (considering a contact angle of 140° between molten Au and $SiO_2$). The gap G between the two structures 18' will be reduced from 50 nm to 24 nm.

In another non-limiting example, two Ag cubes, each 100 nm in size (i.e., 100 nm length, width and height), are established (e.g., via lithography) on a sapphire ($Al_2O_3$) surface 50 nm apart. Exposing these cube structures 14, 18 to heating causes them to melt into two spherical shaped particles 14, 18', each with a radius of 64 nm (considering a contact angle of 130° between molten Ag and $Al_2O_3$). The gap G between the two structures 18' will be reduced from 50 nm to 22 nm.

In a third non-limiting example, two Al cubes, each 100 nm in size (i.e., 100 nm length, width, and height), are established (e.g., via lithography) on a sapphire ($Al_2O_3$) surface 50 nm apart. Exposing these cube structures 14, 18 to heating causes them to melt into two spherical shaped particles 14, 18', each with a radius of 73 nm (considering a contact angle of 82° between molten Al and $Al_2O_3$). The gap G between the two structures 18' will be reduced from 50 nm to 4 nm.

Figures 5A, 5B:
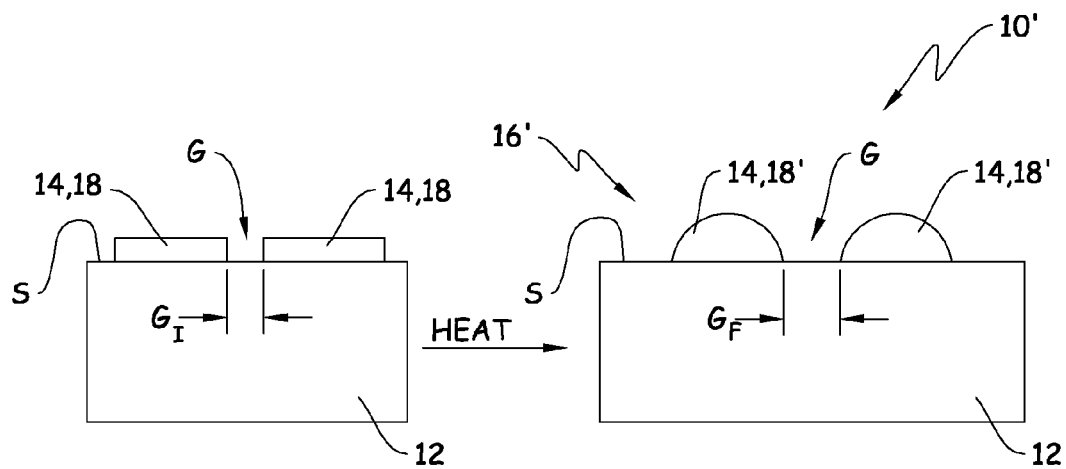
FIGS. 5A and 5B are schematic side views illustrating another embodiment of a metal established on a substrate (FIG. 5A), and the device formed after heating of the metal (FIG. 5B)

Referring now to FIGS. 5A and 5B, another embodiment of the method of forming the device 10' is schematically depicted using side views. As shown in FIG. 5A, the substrate 12 and metal 14 are selected, and the metal 14 is established to form segments 18. Unlike FIGS. 2A and 2B and 3A and 3B, in this embodiment, the substrate 12, metal 14, and initial geometry are selected so that when exposed to heating, the gap G increases in size. The interaction between the materials 12, 14 causes the metal 14 to essentially build upon itself (again, the metal volume does not change), thus increasing in height/thickness and increasing the gap G between the segments 18. As a result, in this embodiment of the antenna 16', the segments 18' are thicker than the initial segments 18, and the final gap size $G_F$ between the segments 18' is larger than the initial gap size $G_I$.

If the desired final gap size $G_F$ is equivalent to the gap size when the metal 14 and substrate 12 are in an equilibrium state, heating may be accomplished until a change in the geometry is no longer observed. In other embodiments, heating may be stopped prior to reaching equilibrium. This may be accomplished when the desired final gap size $G_F$ is equivalent to a gap size that is smaller than the size of the gap G corresponding with the equilibrium state.

In a non-limiting example, two Ag rectangular cubes, each 100 nm in length, 100 nm in width and 20 nm in height, are established (e.g., via lithography) on a sapphire ($Al_2O_3$) surface 50 nm apart. Exposing these rectangular cube structures 14, 18 to heating causes them to melt into two spherical shaped particles 14, 18', each with a radius of 38 nm (considering a contact angle of 130° between molten Ag and $Al_2O_3$). The gap G between the two structures 18' will be increased from 50 nm to 74 nm.

As illustrated in at least some of the examples given herein, whether the gap G is increased or decreased after heating depends, at least in part, on the initial volume and aspect ratio of the metal segment 14, 18. If the metal segment 14, 18 is narrow and tall (i.e., the height is greater than both the length and width), upon heating, the metal 14 tends to reduce in height and become wider in length and/or width. As a result, in this embodiment, the gap G decreases. However, if the metal segment 14, 18 is wide and short (i.e., the height is smaller than both the length and width), upon heating, the metal 14 tends to increase in height and become narrower in length and/or width. As a result, in this embodiment, the gap G increases. The behavior of the metal 14 may be determined by knowing the metal volume (which is conserved after heating), the contact angle θ of the metal 14 to the substrate 12, and that after heating, the metal segment 14, 18' will have a spherical shape (which, in some instances, is truncated).

In any of the embodiments of the device 10, 10' disclosed herein, a physical or chemical template may be incorporated in or on the substrate 12 in order to partially control the final geometry of the segments 18'. The addition of such template(s) allows the re-shaping of the geometry from the initial shape to the final shape to be guided in a particular manner. Examples of physical templates include trenches or rails etched into the substrate 12. Such physical templates define boundaries for the final geometry of the segments 18'. Examples of chemical templates include the addition of surfactants or other materials with desirable wetting properties to the surface S in a predefined manner. Since the metal 14 may react with the treated portions of the surface S differently than the untreated portions of the surface S, the chemical templates also define boundaries for the final geometry of the segments 18'. As a non-limiting example, the physical and/or chemical templates may be used to guide the metal from segments 18 having a circular geometry to segments 18' having an elliptical geometry.

Figure 6A:
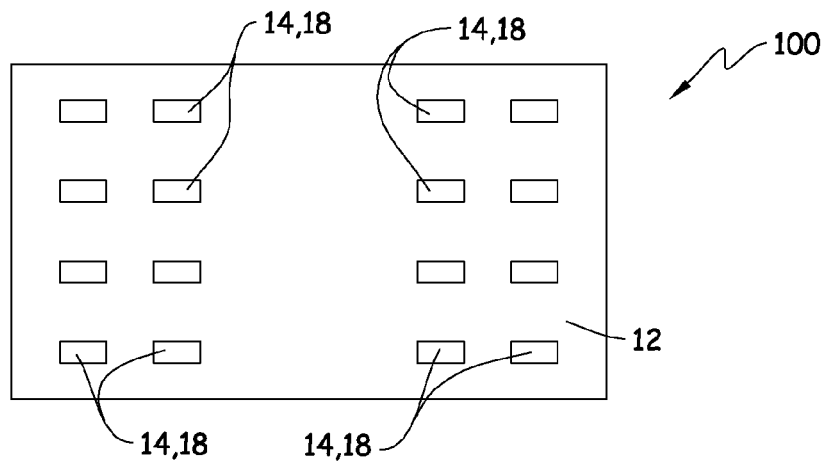
FIGS. 6A and 6B are schematic top views of metal established on a substrate (FIG. 6A), and the array of antennas formed after heating of the metal (FIG. 6B)
Figure 6B:
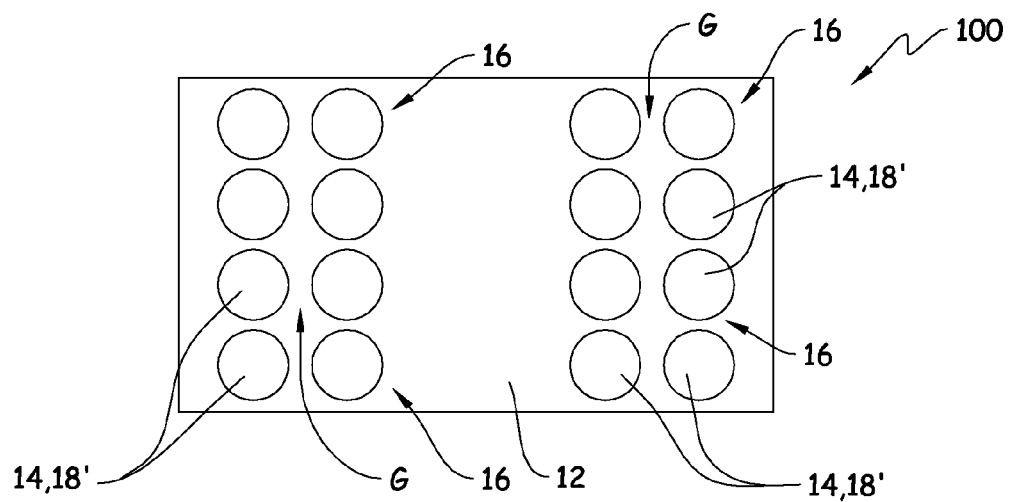

FIGS. 6A and 6B illustrate the top views of an array 100 both before the metal segments 14, 18 are exposed to heating (FIG. 6A), and after the formation of the antennas 16 (FIG. 6B). While antenna 16' is not shown in FIGS. 6A and 6B, it is to be understood that the array 100 could be configured to include antenna 16 and/or antenna 16'. As illustrated in FIG. 6A, multiple metal segments 18 are established on the substrate 12 using one of the techniques previously described. The metal 14 used for a single pair of segments 18 (i.e., those segments that ultimately form a single antenna 16) is generally the same. However, the metal 14 used for one pair of segments 18 (one antenna 16) may be different from the metal 14 used for one or more other pairs of segments 18 (another antenna 16). After exposure to heat, the metal 14 flows to form the spherical shaped segments 18' and the antennas 16. As such, the array 100 includes multiple antennas 16 incorporated onto a single substrate 12. In the embodiment shown, each of the antennas 16 has the same gap size. By selecting the same metal 14 for each of the segments 18, the array 100 includes the plurality of antennas 16 that resonates at the same frequency. It is to be understood that one or more of the antennas 16 may be formed to have a different gap size than another of the antennas 16 and thus different antennas 16 may be configured to resonate at different frequencies.

Figure 7:
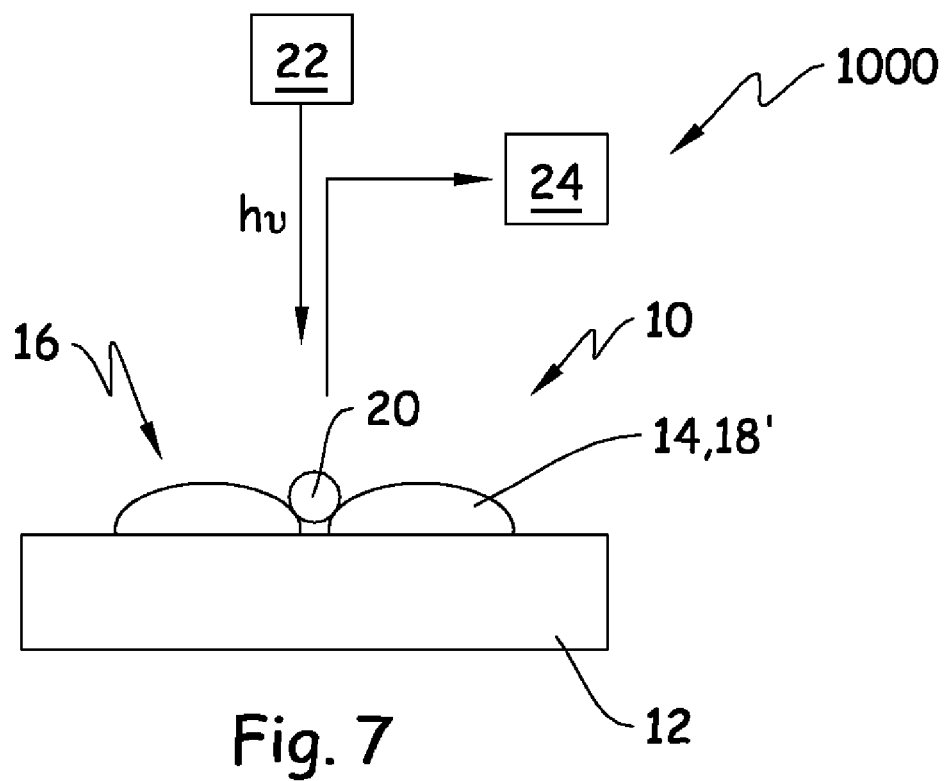
FIG. 7 is a schematic diagram of a system including an embodiment of the optical device.

The devices 10, 10' disclosed herein are suitable for use in standard Raman detection procedures. The system 1000 for such a procedure is shown schematically in FIG. 7 and includes the device 10 having a material of interest 20 (e.g., analyte molecules or particles) positioned in or near the gap G. The system 1000 further includes a stimulation/excitation light source 22 and a detector 24. The material of interest 20 is subsequently subjected to laser excitation of suitable stimulating/exciting wavelengths from the light source 22. This light excites the material of interest 20, and the resulting Raman signals are detected using known detector(s) 24.

The embodiments of the antennas 16, 16' disclosed herein have dynamically controllable (until equilibrium is reached) gaps G, and as such, the plasmonic properties and the magnitude of the field strength between the gap G of the devices 10, 10' may be tuned for a desirable application. This provides an element of control both throughout fabrication, and in some instances, after fabrication and use. Heating may also smooth out the surface of the resulting antenna 16, 16'.

While several embodiments have been described in detail, it will be apparent to those skilled in the art that the disclosed embodiments may be modified. Therefore, the foregoing description is to be considered exemplary rather than limiting.

What is claimed is:

1. An optical device for surface enhanced Raman spectroscopy, comprising:
   a substrate; and
   at least one antenna established on the substrate, the at least one antenna including:
      at least two segments, each segment formed of a metal having a predetermined volume and a predetermined contact angle with respect to the substrate; and
      a gap located between the two segments, the gap having a controllable size such that the at least one antenna resonates at a predetermined frequency that corresponds with the gap, the gap size being controllable via heating until the at least two segments and the substrate are in a state of equilibrium.

2. The optical device as defined in claim 1 wherein each of the at least two segments has a predetermined geometry that is at least partially controlled by the predetermined contact angle.

3. The optical device as defined in claim 2 wherein the substrate includes a physical template or a chemical template that is configured to at least partially control the predetermined geometry of each of the at least two segments.

4. The optical device as defined in claim 1 wherein the gap has an initial size and a final size, and wherein the final size is smaller than the initial size.

5. The optical device as defined in claim 4 wherein the initial size is formed via lithography, wherein the final size is formed via heating of the two segments, and wherein the final size is smaller than that achievable via lithography.

6. The optical device as defined in claim 1 wherein the gap has an initial size and a final size, and wherein the final size is larger than the initial size.

7. The optical device as defined in claim 1, further comprising
at least one other antenna established on the substrate, the at least one other antenna including:
at least two other segments, each other segment formed of a metal having a predetermined volume and an other predetermined contact angle with respect to the substrate, wherein the other predetermined contact angle is different from the predetermined contact angle of the at least one antenna; and
an other gap located between the two other segments, the other gap having a controllable size such that the at least one other antenna resonates at a predetermined frequency that corresponds with the other gap.

8. A method for making an optical device for surface enhanced Raman spectroscopy, comprising: selecting a metal having a predetermined contact angle with respect to a substrate; establishing the metal on the substrate to form at least two segments having a gap therebetween, each of the at least two segments having an initial geometry and a predetermined volume, and the gap having an initial size; and heating the at least two segments, thereby i) altering the initial geometry of each of the at least two segments to achieve a final geometry while maintaining the predetermined volume of each of the at least two segments, and ii) altering the initial size of the gap to achieve a final size that is different than the initial size, the gap size being controllable via heating until the at least two segments and the substrate are in a state of equilibrium.

9. The method as defined in claim 8 wherein establishing the metal on the substrate to form the two segments is accomplished via a lithography technique.

10. The method as defined in claim 8 wherein heating is accomplished isothermally or transiently.

11. The method as defined in claim 8 wherein prior to establishing the metal, the method further comprises forming a physical template or a chemical template on a surface of the substrate, wherein the physical template or chemical template is configured to at least partially control the final geometry of each of the at least two segments.

12. The method as defined in claim 8, further comprising tuning at least a plasmonic resonance of the optical device by controlling the predetermined contact angle.

13. The method as defined in claim 8 wherein heating causes the at least two segments to reduce the initial gap size.

14. The method as defined in claim 8 wherein heating causes the at least two segments to increase the initial gap size.

15. An optical system for surface enhanced Raman spectroscopy, comprising:
an optical device, including:
a substrate; and
at least one antenna established on the substrate, the at least one antenna including:
at least two segments, each segment formed of a metal having a predetermined volume and a predetermined contact angle with respect to the substrate; and
a gap located between the at least two segments, the gap having a controllable size such that the at least one antenna resonates at a predetermined frequency that corresponds with the gap, the qap size being dynamically controllable via heating until the at least two segments and the substrate are in an equilibrium state;
a light source operatively configured to direct light toward the gap; and
a detector operatively positioned to detect an enhanced Raman signal from a material of interest positioned at a region proximate to the gap.

16. The optical system as defined in claim 15, further comprising
at least one other antenna established on the substrate, the at least one other antenna including:
at least two other segments, each other segment formed of a metal having a predetermined volume and an other predetermined contact angle with respect to the substrate, wherein the other predetermined contact angle is different from the predetermined contact angle of the at least one antenna; and
an other gap located between the two other segments, the other gap having a controllable size such that the at least one other antenna resonates at a predetermined frequency that corresponds with the other gap.

* * * * *

UNITED STATES PATENT AND TRADEMARK OFFICE
CERTIFICATE OF CORRECTION

| | |
|---|---|
| PATENT NO. | : 8,134,702 B1 |
| APPLICATION NO. | : 12/574379 |
| DATED | : March 13, 2012 |
| INVENTOR(S) | : David A. Fattal et al. |

It is certified that error appears in the above-identified patent and that said Letters Patent is hereby corrected as shown below:

In column 8, line 25, in Claim 15, delete "qap" and insert -- gap --, therefor.

Signed and Sealed this
Sixth Day of November, 2012

David J. Kappos
*Director of the United States Patent and Trademark Office*